(12) United States Patent
Shao

(10) Patent No.: US 10,578,554 B2
(45) Date of Patent: Mar. 3, 2020

(54) SPECTRUM-SCANNED SPR IMAGING DETECTION SYSTEM

(71) Applicant: SHENZHEN UNIVERSITY, Shenzhen (CN)

(72) Inventor: Yonghong Shao, Shenzhen (CN)

( * ) Notice: Subject to any disclaimer, the term of this patent is extended or adjusted under 35 U.S.C. 154(b) by 0 days.

(21) Appl. No.: 16/504,964

(22) Filed: Jul. 8, 2019

(65) Prior Publication Data

US 2019/0331599 A1 Oct. 31, 2019

Related U.S. Application Data

(60) Division of application No. 15/992,182, filed on May 30, 2018, now Pat. No. 10,393,657, which is a
(Continued)

(30) Foreign Application Priority Data

Jan. 26, 2016 (CN) .......................... 2016 1 0053230

(51) Int. Cl.
 *G01N 21/552* (2014.01)
(52) U.S. Cl.
 CPC ......... *G01N 21/554* (2013.01); *G01N 21/553* (2013.01); *G01N 2201/063* (2013.01); *G01N 2201/10* (2013.01)
(58) Field of Classification Search
 CPC ............... G01N 21/554; G01N 21/553; G01N 21/6458; G01N 21/255; G01N 21/27;
(Continued)

(56) References Cited

U.S. PATENT DOCUMENTS 6,330,062 B1 * 12/2001 Corn ...................... G01N 21/35
 356/445
6,570,657 B1 * 5/2003 Hoppe ..................... G01J 3/04
 356/445
(Continued)

FOREIGN PATENT DOCUMENTS

CN 1393689 A 1/2003
CN 101477045 A 7/2009
(Continued)

OTHER PUBLICATIONS

Internation Search Report of PCT/CN2016/107235, dated Mar. 2, 2017.

*Primary Examiner* — Sang H Nguyen
(74) *Attorney, Agent, or Firm* — W&K IP

(57) ABSTRACT

The present invention provides a surface plasmon resonance (SPR) detection system. This system utilizes a detection light path to form a detection image containing incident angle information and wavelength information. During testing, full-spectrum scan is performed first to obtain a resonance wavelength of a sample. Then, partial-spectrum scanning is performed by continuously tracking the resonance wavelength, and the number of scanning points in each scanning cycle is controlled according to specific situation to shorten the scanning time, thereby obtaining the resonance wavelength of the sample in real time. When the refractive index of the sample changes, the corresponding resonance wavelength changes as well; by obtaining the change of the resonance wavelength, variation of the reflective index of the sample is calculated, which is rapid SPR detection of wavelength modulation.

4 Claims, 6 Drawing Sheets

Related U.S. Application Data continuation of application No. PCT/CN2016/107235, filed on Nov. 25, 2016.

(58) Field of Classification Search
CPC ......... G01N 2201/10; G01N 2201/063; G01N 2201/06113; G01N 2201/064
See application file for complete search history.

(56) References Cited

U.S. PATENT DOCUMENTS

| | | | |
|---|---|---|---|
| 7,193,711 B2* | 3/2007 | Rassman | G01N 21/21 356/369 |
| 8,193,516 B2* | 6/2012 | Kimura | G01N 21/648 250/458.1 |
| 9,006,686 B2 | 4/2015 | Wada | |
| 2001/0026943 A1 | 10/2001 | Dickopf et al. | |
| 2004/0130723 A1* | 7/2004 | Yager | G01N 21/553 356/445 |
| 2006/0023221 A1* | 2/2006 | Kimura | G01N 21/553 356/445 |
| 2006/0092424 A1* | 5/2006 | VanWiggeren | G01N 21/553 356/445 |
| 2009/0086211 A1* | 4/2009 | Dosaka | G01N 21/43 356/445 |
| 2010/0045997 A1* | 2/2010 | Hong | G01N 21/554 356/445 |
| 2011/0310383 A1* | 12/2011 | Masson | G01N 21/553 356/319 |
| 2012/0133943 A1* | 5/2012 | Fontaine | G01N 21/553 356/445 |
| 2013/0175457 A1 | 7/2013 | Wada | |
| 2013/0293896 A1* | 11/2013 | Fujimaki | G01N 21/553 356/445 |
| 2015/0211986 A1* | 7/2015 | Kuang | G01N 21/6458 356/369 |

FOREIGN PATENT DOCUMENTS

| | | |
|---|---|---|
| CN | 101865840 A | 10/2010 |
| CN | 105486665 A | 4/2016 |

\* cited by examiner

SPECTRUM-SCANNED SPR IMAGING DETECTION SYSTEM

CROSS-REFERENCE TO RELATED APPLICATIONS

This application is a division application of U.S. patent application Ser. No. 15/992,182 with a filing date of May 30, 2018, and further claims priority to Chinese Patent Application No. 201610053230.3 with a filing date of Jan. 26, 2016. The content of the aforementioned applications, including any intervening amendments thereto, are incorporated herein by reference.

FIELD OF THE INVENTION

The present invention belongs to the technical field of biological detection, and particularly relates to an SPR detection system and method.

BACKGROUND OF THE INVENTION

An SPR (Surface Plasmon Resonance) technique may be used for kinetic parameter measurement of molecular identification, specific reaction and inter-molecular reaction and the like, and has wide application. A spectrum diagnosis SPR technique has a large dynamic range, high sensitivity and involved mature photoelectric equipment, and therefore is broadly researched by domestic and foreign scholars. However, positions of SPR resonance wavelengths cannot be directly and correctly measured. Since corresponding intensity may be equal to zero in theory, region values near zero are basically submerged in noise, and the sensitivity of the SPR technique is extremely sensitive to spectrum resolution capability, the resolution capability of the spectrum position is generally required to reach 0.01 nm. Moreover, with inter-molecular dynamic interaction of a sensing surface, resonance wavelengths will move, a movement magnitude is correlated to concentration of reaction molecules and molecular weights. For an ordinary protein molecule such as IgG, the concentration is 5 ug/ml, the movement range is about 2-3 nm, and reaction time is about 5 minutes. In order to measure a curve of a resonance wavelength varying with reaction time, namely, an SPR spectrum curve, time resolution is generally required to be less than 1 second. Specifically, it is generally required to perform parallel high-flux measurement on the whole two-dimensional sensing surface in fact Since the difference between different positions of the sensing surface may lead different resonance wavelengths of various sites, and therefore how to rapidly diagnose SPR resonance wavelengths of various sites of the whole sensing chip within 1 second is a bottleneck of a spectrum diagnosis SPR technique.

At present, there are two SPR diagnosis methods One method is that high-flux measurement is obtained by sacrificing time; the other method is that high time resolution is obtained by sacrificing measurement flux. The former adopts a monochrometer to scan a wavelength of an incident light and synchronously records light intensity under each wavelength utilizing a two-dimensional detector such as a CCD camera, a series of intensity images are recorded with the scanning of the incident wavelength, different times correspond to different wavelengths, each image corresponds to one wavelength, a corresponding pixel of each image forms a curve of intensity varying with a spectrum, namely, an SPR spectrum outline curve of points on the corresponding sensing surface, analogically, a series of SPR spectrum outline curves are composed of all the pixels according to the above manner, each curve corresponds to one pixel point of the SPR sensing surface, a minimum value of each SPR spectrum outline line is a resonance light wavelength of this pixel point, the change of a refractive index of a sensor surface is obtained by continuously and repeatedly obtaining the above series of SPR spectrum outline curves within the same fixed spectrum range and monitoring the change of the minimum value of each SPR spectrum outline line, so as to achieve SPR sensing measurement. Beam splitting in the monochrometer is achieved by mainly adopting rotary grating, and rapid cyclical scanning cannot be performed due to factors such as a mechanical scanning manner and rotation element inertia; moreover, due to different sensing film thickness and light incident angles (caused by poor white light source collimation, prism dispersion and the like) and inconsistent resonance spectrum of various points of a sensing chip caused by factors such as types and concentrations of probe molecules as well as inconsistent movement generated by inter-molecular interaction, the whole sensing surface cannot be properly set in advance, and therefore, at present, all the reports are that full-spectrum line scanning is performed in a fixed whole working spectrum segment to avoid some resonance wavelengths to be removed out of the scanning range in the process of measurement to generate measurement error. At presents it is reported that the rapidest scanning speed for the spectrum diagnosis SPR is 2 s/wavelength, and thus time for obtaining the whole SPR spectrum outline once is considerably long, and cannot meet dynamic monitoring of inter-molecular interaction.

The later utilizes a spectrometer to perform rapid spectrum analysis of the reflected light and has a sufficiently rapid measurement speed. In order to improve measurement flux, reflected lights at different positions of a sensing film are respectively guided into different spectrometers to achieve parallel detection, but, each position needs one spectrometer, so cost is expensive, and monitoring and imaging detection of a high-density sensing chip cannot be achieved.

In summary, the existing technology has the following technical problems there is no technology to achieve parallel rapid scanning of SPR spectrum curves of all the sites of a two-dimensional sensing chip, the SPR spectrum curves of all the sites of the two-dimensional sensing chip cannot be rapidly obtained, and then rapid parallel monitoring of resonance wavelengths of all the sites of the two-dimensional sensing chip cannot be achieved, and the existing technology also has defects that the consistence of sensing sensitivities of various position points of the two-dimensional sensing chip is poor.

SUMMARY OF THE INVENTION

In view of the defects of the prior art, the object of the present invention is to provide an SPR detection system and method for the purposes that partial spectrum scanning is performed on a resonance spectrum curve near a resonance wavelength, thereby reducing the scanning spectrum range; the resonance spectrum is tracked in real time through feedback of the scanning spectrum range to improve the diagnosis speed of the resonance wavelength; the scanning time of the whole SPR spectrum curve within the traditional broad spectrum range is long (one SPR spectrum is obtained in at least dozens of seconds), and time of some inter-molecular interactions is relatively short, the traditional broad spectrum scanning cannot meet the problem of real-time monitoring of inter-molecular interaction, and this technology aims at solving the problem of real-time monitoring of inter-molecular interaction.

The present invention provides an SPR detection system, comprising a light source which is used for emitting a broadband light having a continuous spectrum; a first collimation lens group which is used for collimating and focusing the broadband light; a multimode fiber (MF) whose incidence end is arranged on an output focal plane of the first collimation lens group and which is used for coupling the light focused by the first collimation lens group, a second collimation lens group whose input focal plane is provided with an emergent end of the multimode fiber MF and which is used for collimating and then focusing the coupled light; a diaphragm DA which is located on the output focal plane of the second collimation lens group and used for performing spatial filtering on the light focused by the second collimation lens group to obtain the focused light, a first lens L5 which is arranged confocal to the second collimation lens group and used for collimating the focused light, a liquid crystal tunable optical filter which is used for filtering the broadband light emitted by the light source to obtain a narrowband light; a polarizing film P1 which is used for polarizing the narrowband light to obtain an incident light being in a polarization state; an SPR sensing unit which includes a prism, a gold film and a flow cell, the prism coupling the incident light and then exciting surface plasmon resonance of the gold film, and the flow cell allowing a to-be-detected sample to pass through the surface of the gold film, thereby performing detection; a second lens L6 which is used for collecting and collimating a light reflected by the SPR sensing unit, an analyzer P2 which is used for eliminating a stray light in the reflected light to improve a signal-to-noise ratio, a third lens L7 which is used for converging the polarized light; an area array detector which is disposed on the focal plane of the third lens L7 and used for recording the intensity of the spectrum after converge, a control module whose input end is used for receiving and processing the image of the light collected by the area array detector, and then outputting a feedback control signal for adjusting the scanning spectrum range of the liquid crystal tunable optical filter.

Further, the first collimation lens group successively includes a first collimation lens L1 and a second collimation lens L2 which are coaxially arranged.

Furthermore, the second collimation lens group successively includes a third collimation lens L3 and a fourth collimation lens L4 which are coaxially arranged.

Furthermore, when working, after the spectrum scanning range is determined, the liquid crystal tunable optical filter performs spectrum scanning output according to a designated working mode, the area array detector simultaneously records the intensity of the light reflected by an SPR sensing unit corresponding to each output spectrum and obtains a plurality of intensity images, and pixels of the same position of each image form a curve of intensity varying with a light wavelength, namely, an SPR spectrum outline curve of this position.

Through the above technical solution conceived by the present invention, compared with the prior art, since this technology can rapidly scan any partial spectrum regions and automatically changes the scanning spectrum range according to the change of the SPR resonance wavelength, rapid spectrum SPR detection of a two-dimensional array is achieved, interaction of a plurality of biomolecules can be simultaneously monitored in real time, and this technology has the advantages of high flux and rapid detection.

DETAILED DESCRIPTION OF THE EMBODIMENTS

Figure 1:
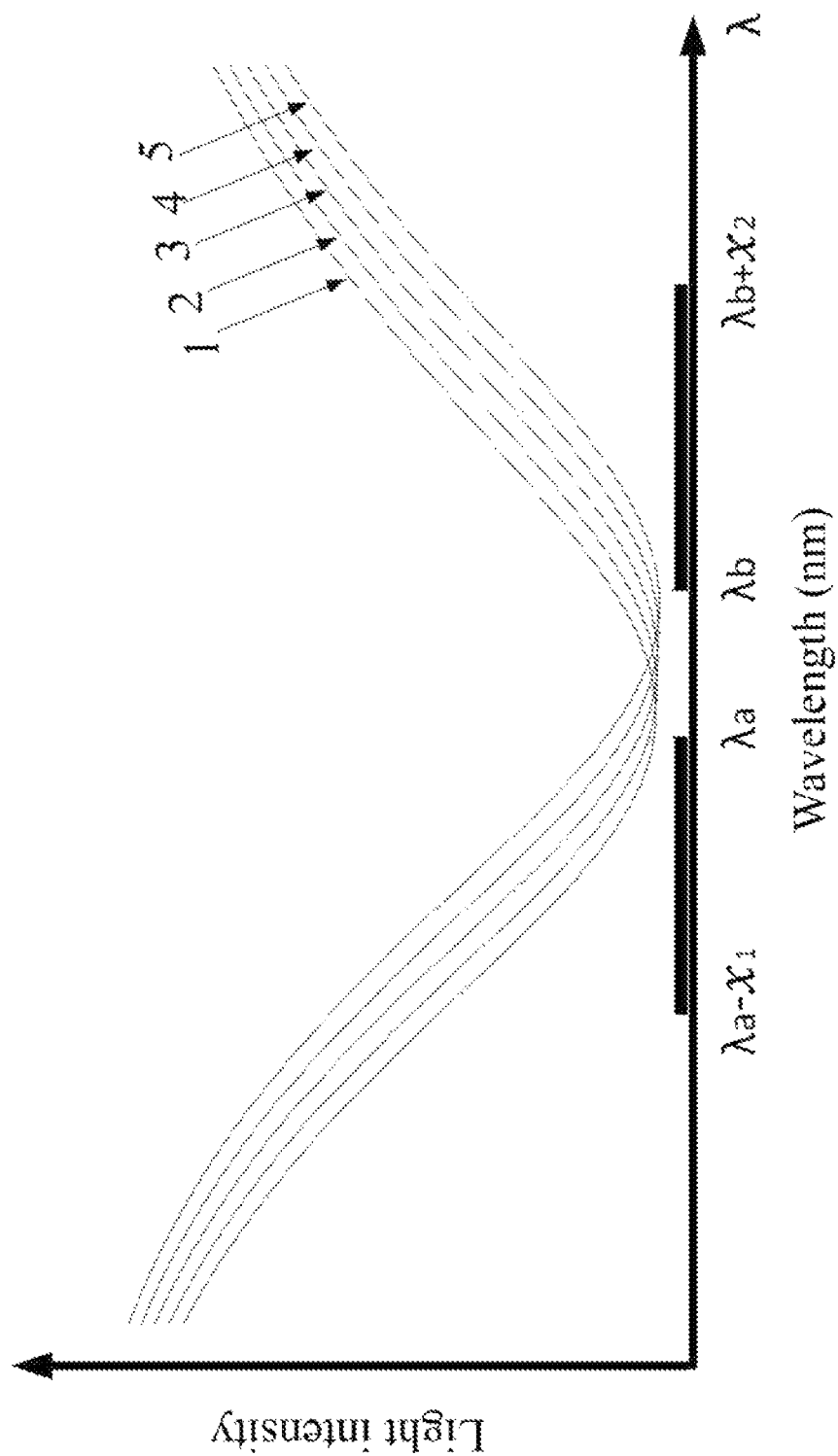
FIG. 1 illustrates a complete SPR spectrum curve; wherein, $\lambda_a$ and $\lambda_b$ are minimum and maximum resonance wavelengths respectively, and $\chi_1$ and $\chi_2$ are constants.
Figure 2:
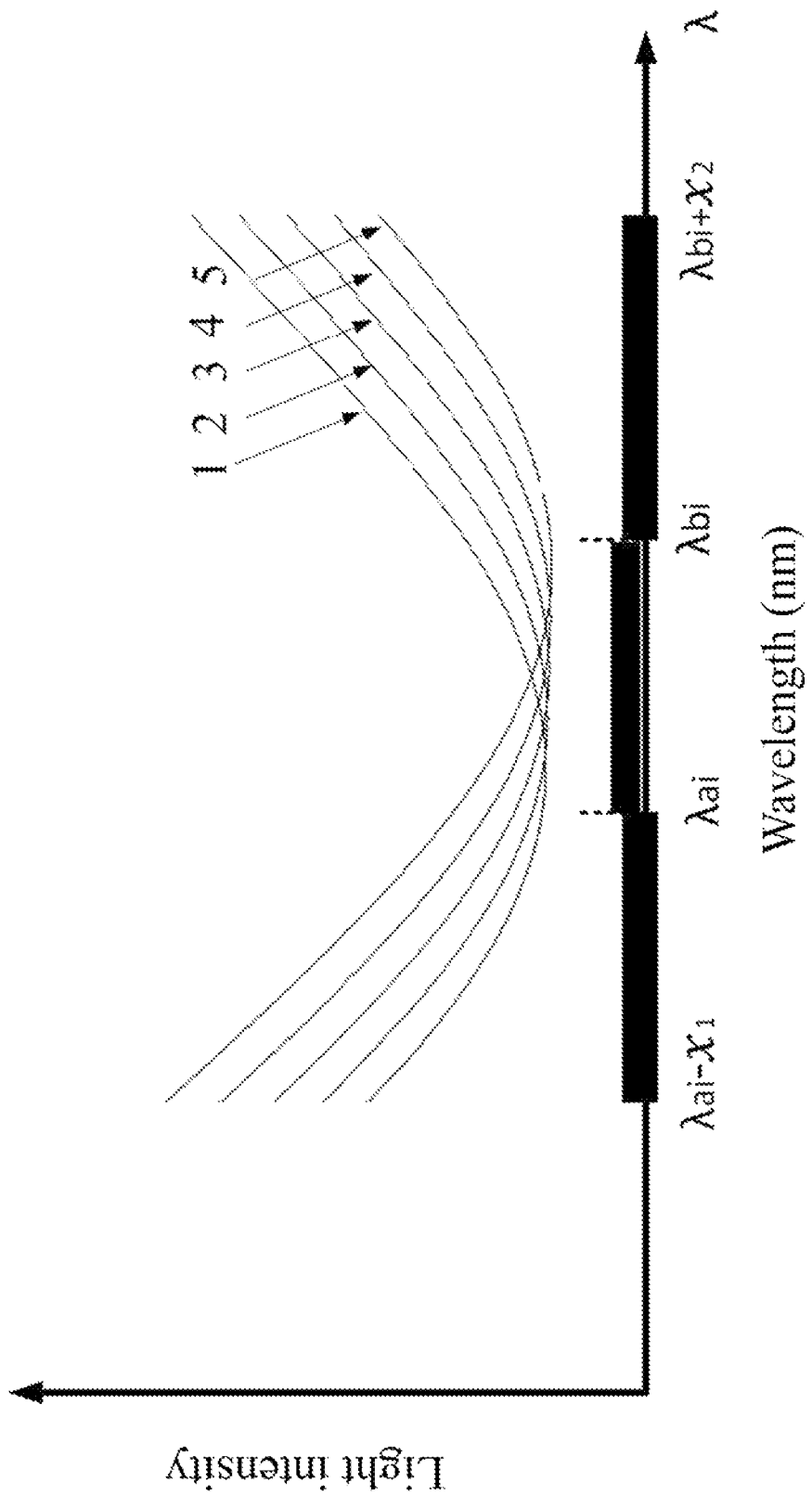
FIG. 2 illustrates a partial SPR spectrum curve; wherein, $\lambda_{ai}$ and $\lambda_{bi}$ are minimum and maximum resonance wavelengths respectively, and $\chi_1$ and $\chi_2$ are constants.

To make the object, the technical solution and the advantages of the present invention more apparent and understandable, the present invention will be further described in detail in combination with drawings and embodiments. It should be understood that embodiments described here are only for explaining the present invention but not limiting thereto.

According to the present invention, as to partial spectrum scanning of a resonance spectrum curve near a resonance wavelength, the scanning spectrum range is reduced. However, the currently existing fixed scanning range is adopted, if a small spectrum scanning range proposed by us is selected and this range is fixed invariably, the resonance wavelength needing to be detected will gradually go beyond the scanning range and is not detected with proceeding of biological reaction. As to this point, the present invention also proposes a scanning spectrum range feedback technology to track the resonance spectrum in real time and improve the diagnosis speed of the resonance wavelength.

The present invention provides a step-size-tunable partial feature spectrum scanning technology having a function of scanning range feedback By this technology, spectrum subintervals containing resonance wavelengths near resonance wavelengths are only scanned, the current scanning spectrum range is determined through the maximum resonance wavelength and the minimum resonance wavelength in all the resonance wavelengths measured last time, then the maximum resonance wavelength and the minimum resonance wavelength in all the resonance wavelengths are sought according to the obtained current scanned SPR spectrum outline, and then the scanning spectrum range of next scanning is determined. The process is continuously and repeatedly performed, so that all the SPR wavelengths can be dynamically tracked.

Meanwhile, in order to ensure that all the resonance wavelengths are constantly within the scanning range, when the scanning range is determined each time, one wavelength range extends toward a long wavelength direction at the obtained maximum resonance wavelength, one wavelength range extends toward a short wavelength direction at the minimum resonance wavelength, a new wavelength range is formed as the scanning range after extension, and the extended wavelength range can be set according to a final SPR partial spectrum curve obtaining time, and can be large or small, with extreme flexibility. This obtaining time is proportional to a product of scanning wavelength number and scanning time of each wavelength, the larger the extension range is, the longer the obtaining time is. Since diagnosis precision of the resonance wavelength is mainly influenced by the spectrum scanning range and scanning point density near the resonance point, we also propose a step-size-flexible tunable scanning technology, precise scanning of the small step size (≤2 nm) is adopted near the resonance point to improve scanning precision and late data processing precision, coarse scanning of the large step size (>2 nm) is adopted in a region depart from the resonance point to improve the scanning speed, thereby not only ensuring the region but also achieving high precision. Specifically, a scanner adopts a molecular mechanism tunable filter which rapidly responds, can complete output wavelength switching within tens of milliseconds even shorter time, and can electrically control switching of scanning regions and step sizes. In order to ensure achievement of the above method, the filter mainly includes a liquid crystal tunable optical filter, an electro-optical tunable optical filter, an acoustic-optical tunable optical filter, an F-P tunable optical filter and the like at present.

Specific steps comprise:

(1) parallel scanning and recording a two-dimensional image of a sensing chip of a corresponding wavelength in an equal step size manner on the whole working spectrum segment (550 nm-750 nm), as shown in FIG. 1;

(2) forming a spectrum-intensity curve by corresponding pixels of the obtained image so as to form a series of SPR complete spectrum curves, or calculating an average value on partial adjacent pixels of the image obtained in step 1 to form a new two-dimensional image having a fewer pixel, and then forming a spectrum-intensity curve by corresponding pixels of the new formed two-dimensional image, thereby obtaining an SPR spectrum curve having a higher signal-to-noise ratio;

(3) through fitting and interpolating in turn, respectively obtaining a minimum intensity value of each SPR spectrum curve, namely, a resonance wavelength of a corresponding sensing position;

(4) comparing a maximum resonance wavelength and a minimum resonance wavelength of all the obtained resonance wavelengths;

(5) moving the maximum resonance wavelength toward a long wavelength direction by a distance, wherein the wavelength at this moment is a wavelength upper limit of the next-scanning region; and moving the minimum resonance wavelength toward a short wavelength direction by a distance, wherein the wavelength at this moment is a wavelength lower limit of the next-scanning region, so far, determining that a next-scanning wavelength range is a range from the wavelength upper limit to the wavelength lower limit; wherein, a distance of moving toward the long wavelength direction and a distance of moving toward the short wavelength direction may be identical or different, and are between 3 nm~50 nm in general;

(6) determining a scanning step size, wherein, a step size within a wavelength range between the maximum resonance wavelength and the minimum resonance wavelength is a small step size such as 0.01 nm-2 nm, a large step size such as 3 nm-20 nm is adopted beyond this region; and the step size may vary;

(7) performing partial rapid scanning within the wavelength range determined in step 4 and recording a corresponding two-dimensional image, wherein, similar to step 1, the scanning range and the scanning step size are just different.

(8) performing steps 2-7 on partial-scanning images to continuously obtain resonance wavelengths of all sensing positions at different times to form a curve of a resonance wavelength varying with time. Alternatively, change of the resonance wavelength of each sensing position is used as a pixel value so as to obtain a two-dimensional wavelength-sensitive SPR sensing image.

Figure 3:
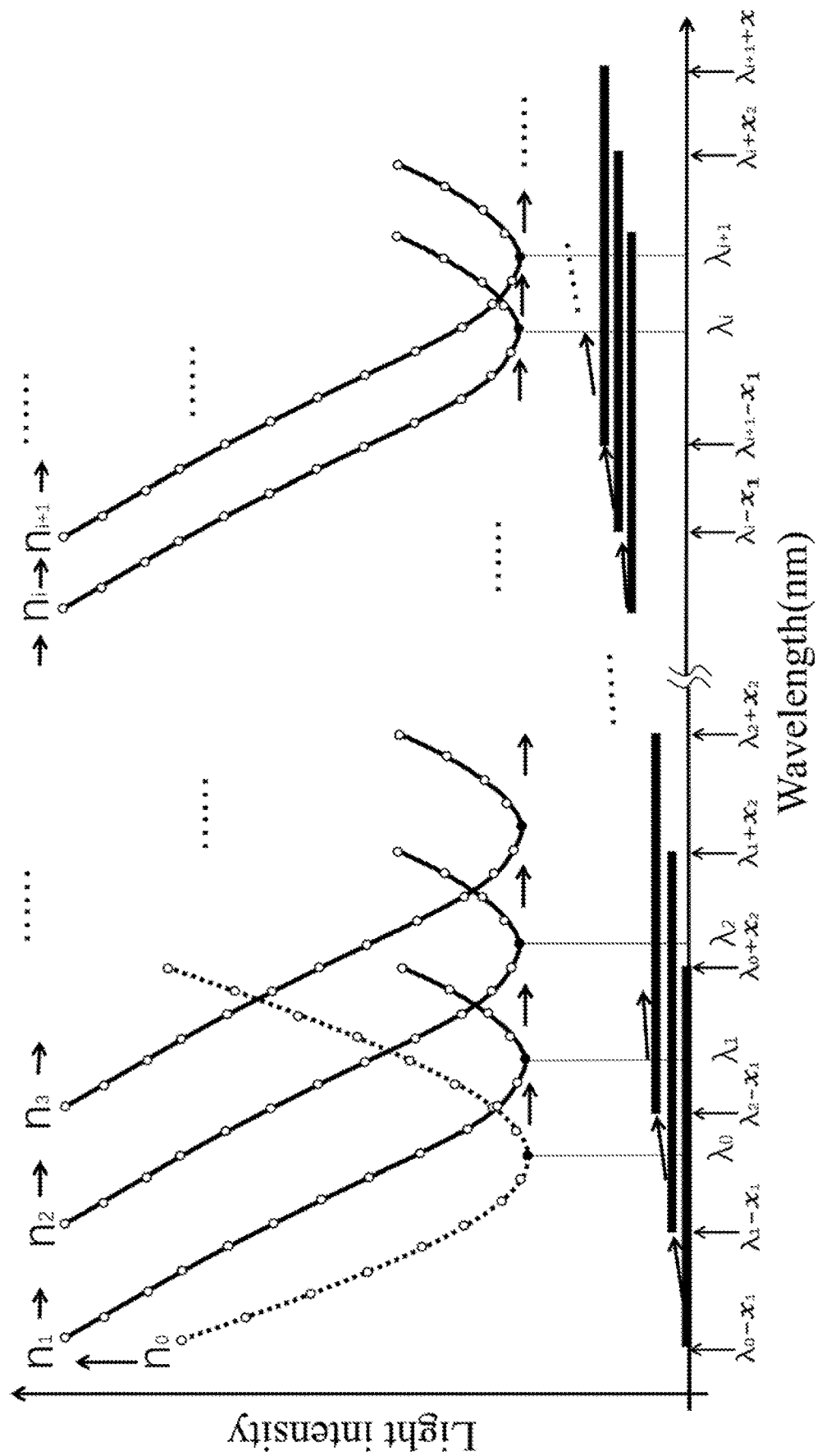
FIG. 3 is a resonance wavelength tracking diagram.

In order to simplify image analysis, we take single points as examples to further illustrate a resonance wavelength tracking process. The resonance wavelength tracking process as shown in FIG. 3, the reflective index of the sensing surface will change with inter-molecular interaction of the sensing surface, and curves 1-$k$ respectively represent partial SPR spectrum curves obtained by scanning at different times. A partial-scanning range when reaction starts is $[\lambda_0-\chi_1, \lambda_0+\chi_2]$, and a corresponding partial SPR curve is a curve 1 (point line); when the change of the reflective index allows the resonance wavelength to move from $\lambda_0$ to $\lambda_1$, at this moment, a corresponding scanning interval will automatically change into $[\lambda_1-\chi_1, \lambda_1+\chi_2]$ as well; a corresponding partial SPR curve is a curve 2, at this moment, the change of the reflective index allows the resonance wavelength to move from $\lambda_1$ to $\lambda_2$, at this moment, a corresponding scanning interval will automatically change into $[\lambda_2-\chi_1, \lambda_2+\chi_2]$, and a corresponding partial SPR curve is a curve 3. According to this rule, the method is cycled repeatedly. Resonance wavelength tracking is achieved through a scanning feedback method.

Figure 4:
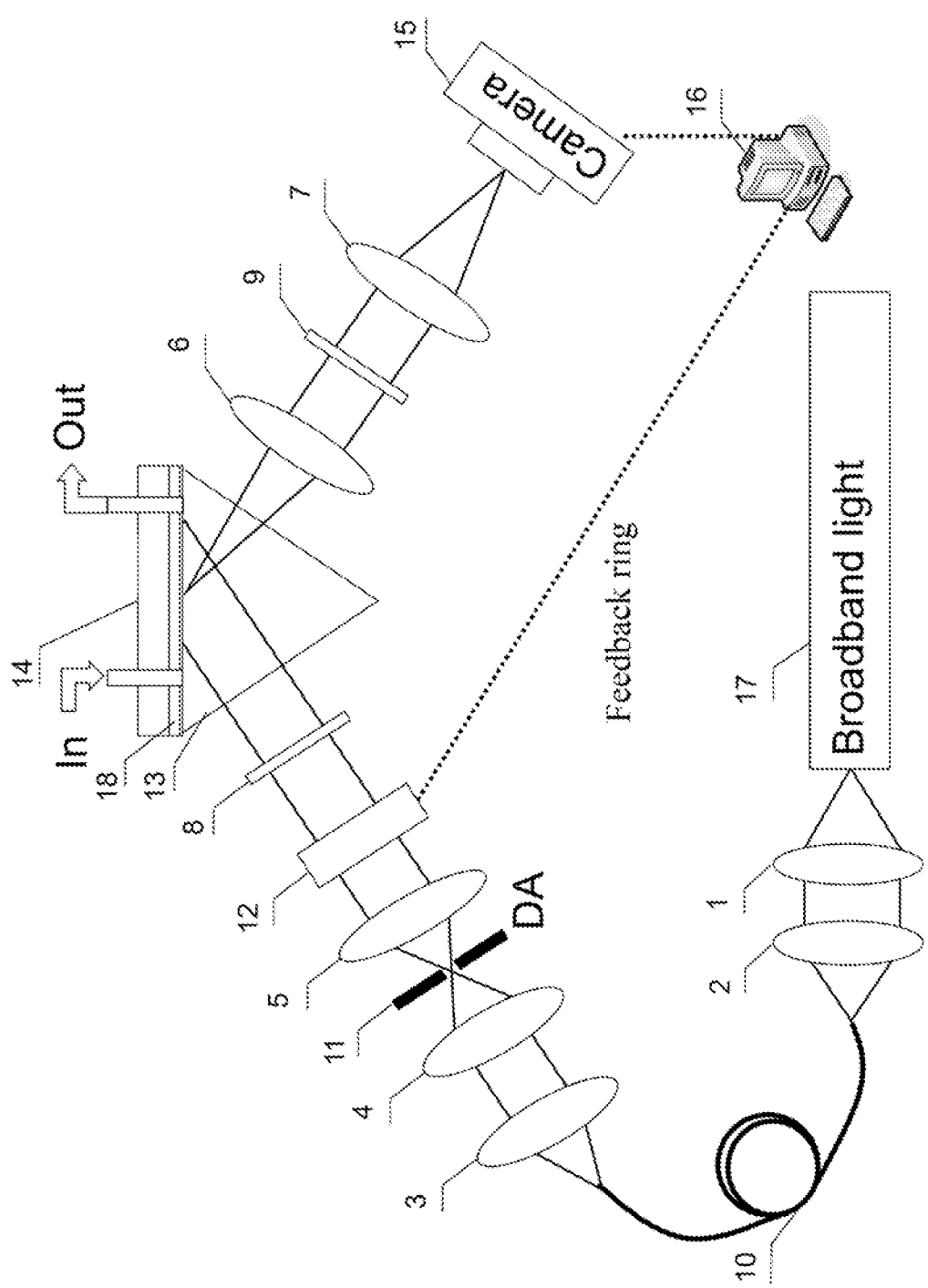
FIG. 4 is a principle diagram of a spectrum diagnosis SPR imaging system.

The present invention also provides an SPR detection system whose structure is as shown in FIG. 4. The SPR detection system includes: an optical fiber output broadband light source Halogen Lamp, a collimation lens group (L1, L2), a rapid tunable optical filter MF, a polarizer, an SPR sensing unit, an imaging lens group, an analyzer and an area array detector.

The broadband light source is a halogen lamp, a white light source and a light source generated by laser exciting fluorescent powder and emits a broadband light being 550 nm-800 nm and having a continuous spectrum; a first collimation lens L1 and a second collimation lens L2 are the collimation lens group and couple the light emitted by the light source into a multimode fiber MF, the emergent end of the multimode fiber MF is located on the focal plane of a third collimation lens L3, and the emitted light is collected and collimated by and then converged to the focal plane of the third collimation lens L3 again by a fourth collimation lens L4; a diaphragm is located on the focal plane of the fourth collimation lens L4 and only allows the focused light points to pass and block other stray lights so as to take a spatial filtering effect, a first lens L5 and the fourth collimation lens L4 are confocal and are used for collimating the light waves filtered by the diaphragm, the liquid crystal optical filter LCTF is used for electrically controlling rapid filtering of any wavelengths to achieve a narrowband spectrum (0.1-20 nm) scanning output of rapid spectrum non-mechanical movement; the polarizer P1 is used for further improving P light polarization and inhibiting S light, the P polarized lights are coupled by a prism to be irradiated to a thin metal sensing film layer on the surface of the prism, and the P polarized light reflected by the sensing film is collected via a second lens L6 and polarized via the analyzer P2 so that the P polarized light passes, then coupled by the third lens L7 to a CCD camera; the second lens L6 and third lens L7 form an imaging group so that the sensing surface is imaged to the CCD camera. A feedback loop is used for returning a scanning spectrum range and ensuring that a computer can set the scanning spectrum range of the liquid crystal tunable optical filter according to the returned scanning range. After the spectrum scanning range is determined, the liquid crystal tunable optical filter will perform spectrum scanning output according to a designed working mode, the CCD camera simultaneously records the light intensity reflected by the sensing film corresponding to each output spectrum, in such a way, a series of intensity images are obtained, pixels of the same position of each image form a curve of intensity varying with the light wavelength, namely an SPR spectrum outline curve of this position, in such a way, the series of two-dimensional CCD images will form a series of SPR spectrum outline curves, and each pixel of the image corresponds to a sensing site on the surface of the sensing film, and the series of SPR spectrum outline curves correspond to all the sensing sites on the surface of the sensing film.

In embodiments of the present invention, the liquid crystal tunable optical filter has two working modes (1) an equal-step-size scanning mode, namely, within a designed scanning range, the scanning step size is fixed invariably, an output center wavelength is continuously changed to achieve spectrum scanning; (2) a variable-step-size scanning mode, namely, within a designed scanning range, the scanning step size changes, precise scanning is performed in a small step size (such as 0.01 nm-2 nm) in a region near a resonance point to improve the diagnosis precision of the resonance spectrum, and a large step size (such as 3 nm-20 nm) is adopted in a region depart from the resonance point to improve a scanning speed.

According to a series of obtained SPR spectrum outline curves, an SPR resonance wavelength of each curve is diagnosed through data fitting and interpolation algorithms, a new scanning range may be generated according to these resonance wavelengths, and there are many generation methods: (1) a maximum resonance wavelength and minimum resonance wavelength method, namely, a minimum resonance wavelength Lamdamin and a maximum resonance wavelength Lamdamax are sought from these resonance wavelengths, then the maximum resonance wavelength moves toward a long wave direction by a distance (such as 8 nm), namely, a corresponding wavelength is Lamdamax+8, and the minimum resonance wavelength moves toward a short wave direction by a distance (such as 8 nm), namely a corresponding wavelength is Lamdamin−8 (such as 8 nm), that is, a new spectrum scanning range is [Lamdamin−8, Larndamax+8], (2) a resonance wavelength average value method, namely, an average value of all the resonance wavelengths are solved to obtain an average resonance wavelength Lamdaave, the average resonance wavelength moves from a long wave direction by a distance, namely, a corresponding wavelength is Lamdaave+10 nm, the average resonance wavelength moves from a short wave direction by a distance, namely, a corresponding wavelength is Lamdaave−10 nm, that is, a new spectrum scanning range is [Lamdaave−10, Lamdaave+10], here, a movement distance may be determined at random according to measurement time, if rapid measurement is needed, a movement distance of less than 10 nm needs to be selected; if there is no requirement on measurement time, a large movement distance such as 20 nm can be selected.

A new scanning range is reset in the liquid crystal tunable optical filter through a feedback loop so that the filter performs scanning in the new scanning range and then a group of two-dimensional CCD images and a series of corresponding new resonance wavelengths are obtained again, and then a new scanning spectrum range is obtained again. Thus, the above process is cycled to continuously obtain a series of new resonance wavelengths, and interaction detection of biological molecules on the surface of the film may be achieved by monitoring change of resonance wavelengths.

Figure 5:
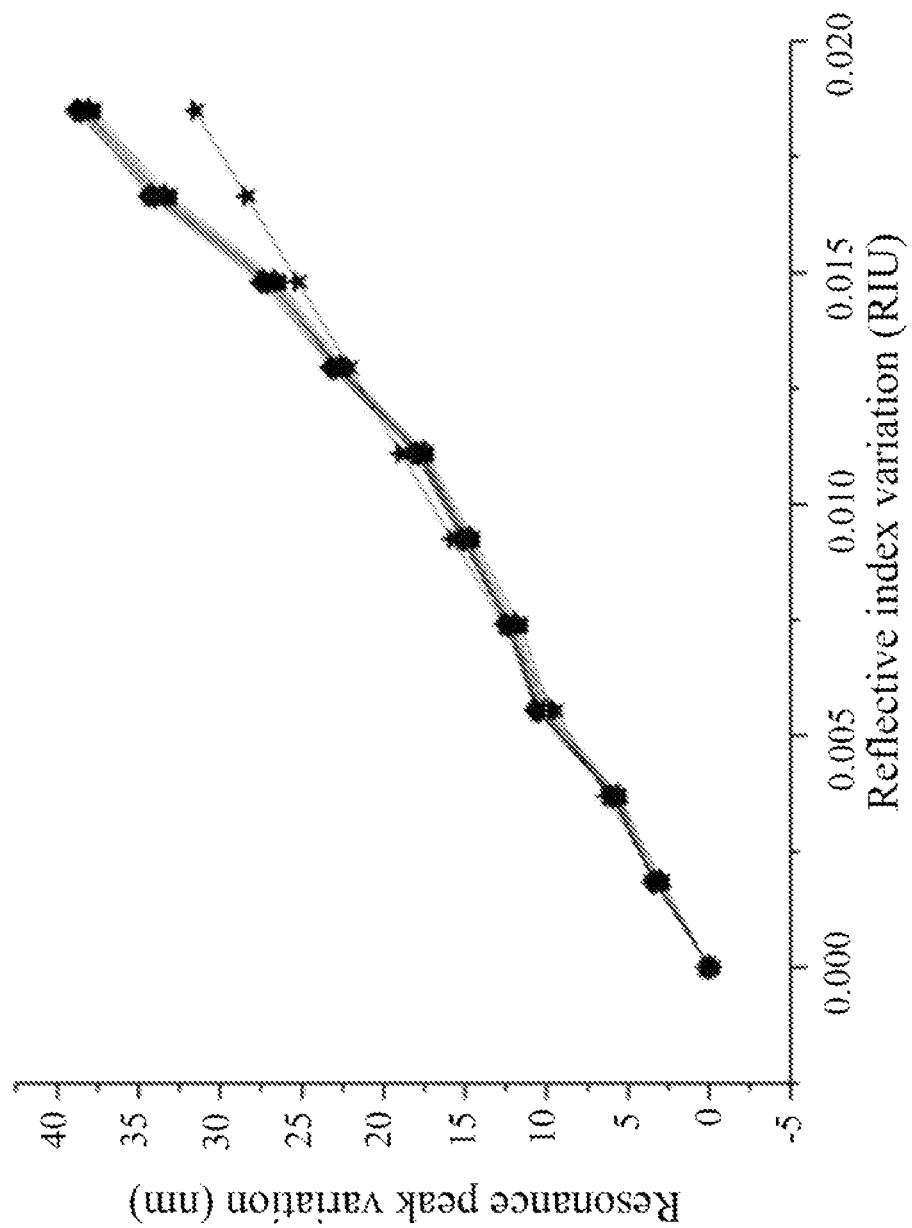
FIG. 5 illustrates dynamic range experiment results.

As shown in FIG. 5, a dynamic range test is performed as to different 9 position points of the sensing chip, and results show that dynamic ranges of various positions are identical and have good consistence.

Figure 6:
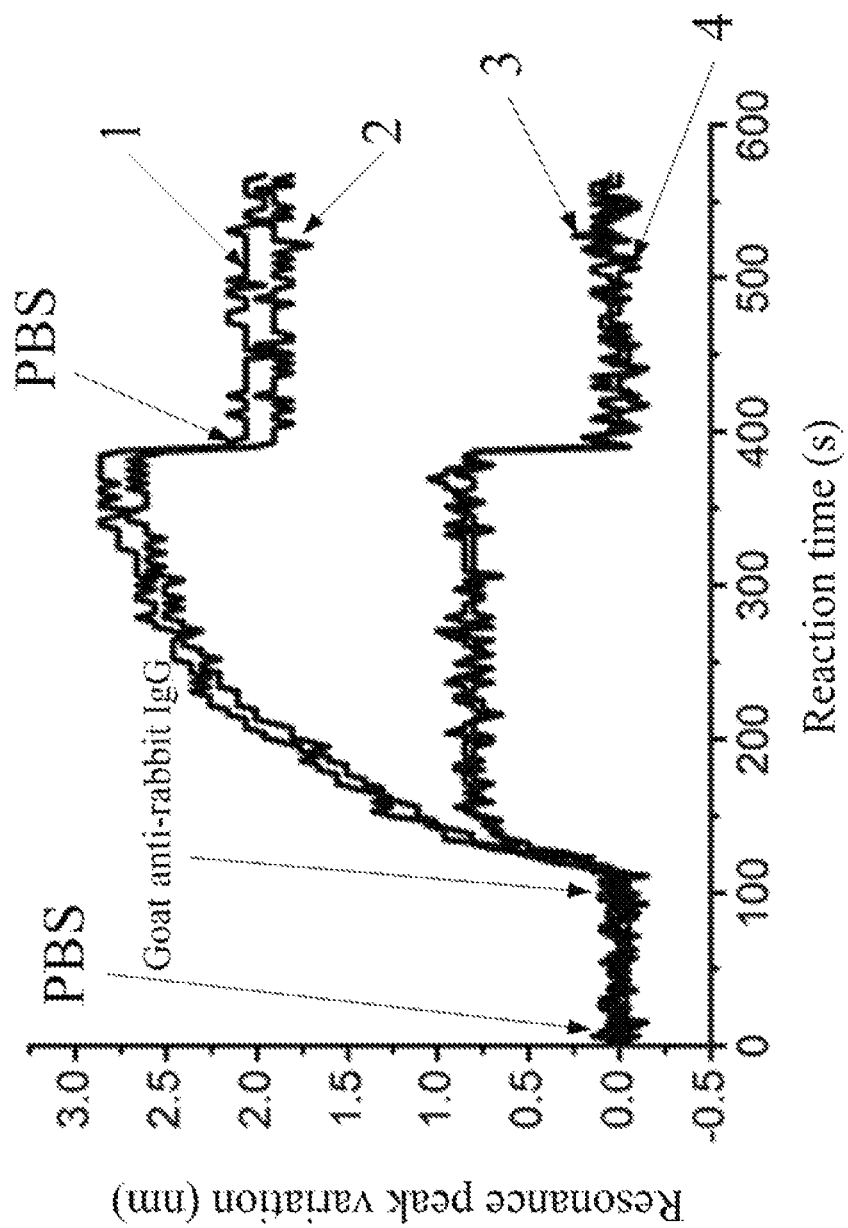
FIG. 6 illustrates protein interaction measurement curves.

In order to more further illustrate the SPR detection device and method provided by embodiments of the present invention, at first, the following detailed description is performed in combination with specific application examples: rabbit IgG protein molecules having the same concentration are modified on two sites of the surface of the sensing film, meanwhile, other any two sites (which are not modified by proteins) are selected as reference, when flowing into PBS buffer solution, no interaction is generated, SPR signals are in a horizontal base line (a first curve segment); when the solution of goat-containing anti-rabbit IgG protein molecules flows through the surface of the sensing film, a corresponding SPR signal generates obvious curve change and then PBS solution is introduced so that the SPR signal curve is changed into a horizontal line segment (a third horizontal line segment), and the amplitude of the horizontal line segment is far higher than that of a starting segment (1, 2 curve segments as shown in FIG. 6), illustrating sites which are modified by rabbit IgG generate inter-molecular interaction. And SPR signals at sites which are not modified by IgG hop to a second horizontal line segment, and then the PBS solution is introduced so that the curve returns back to the horizontal segment (3,4 curve segments as shown in FIG. 6) of the amplitude of the starting stage, illustrating generation of no inter-molecular interaction.

Those skilled in the art easily understand that the above description is only preferred embodiments of the present invention but not limiting the present invention, and any modifications, equivalent substitutions, improvements and the like made within the spirit and principle of the present invention all should be included within the protection scope of the present invention.

We claim:

1. A surface plasmon resonance detection system, comprising
a light source which is used for emitting a broadband light having a continuous spectrum,
a first collimation lens group which is used for collimating and then focusing the broadband light,
a multimode fiber whose incidence end is arranged on an output focal plane of the first collimation lens group and which is used for coupling the light focused by the first collimation lens group;
a second collimation lens group whose input focal plane is provided with an emergent end of the multimode fiber and which is used for collimating and then focusing the coupled light;
a diaphragm which is located on the output focal plane of the second collimation lens group and used for performing spatial filtering on the light focused by the second collimation lens group to obtain the focused lights;
a first lens which is arranged confocal to the second collimation lens group and used for collimating the focused light;
a liquid crystal tunable optical filter which is used for filtering the broadband light emitted by the light source to obtain a narrowband light;
a polarizing film which is used for polarizing the narrowband light to obtain an incident light being in a polarization state;

an SPR sensing unit which includes a prism, a gold film and a flow cell; the prism coupling the incident light and then exciting surface plasmon resonance of the gold film, and allowing a to-be-detected sample to pass through a surface of the gold film by the flow cell, thereby performing detection, a second lens which is used for collecting and collimating the light reflected by the SPR sensing unit;

an analyzer P2 which is used for eliminating a stray light in the reflected light to improve a signal-to-noise ratio;

a third lens L7 which is used for converging the polarized light;

an area array detector which is disposed on a focal plane of the third lens and used for recording the intensity of the spectrum after converging;

a control module whose an input end is used for receiving the image of the light collected by the area array detector and processing the image, then outputting a feedback control signal for adjusting a scanning spectrum range of the liquid crystal tunable optical filter.

2. The SPR detection system of claim 1, wherein, the first collimation lens group successively includes a first collimation lens and a second collimation lens which are coaxially arranged.

3. The SPR detection system of claim 1, wherein, the second collimation lens group successively includes a third collimation lens and a fourth collimation lens which are coaxially arranged.

4. The SPR detection system of claim 1, wherein, when working, after the spectrum scanning range is determined, the liquid crystal tunable optical filter performs spectrum scanning output according to a designated working mode, an intensity of a light reflected by an SPR sensing unit corresponding to each output spectrum is simultaneously recorded by the area array detector and a plurality of intensity images are obtained, pixels of the same position of each image form an SPR spectrum outline curve of this position showing which indicating the intensity varying with a light wavelength.

* * * * *